(12) United States Patent
Boyle et al.

(10) Patent No.: US 7,678,128 B2
(45) Date of Patent: Mar. 16, 2010

(54) DELIVERY AND RECOVERY SHEATHS FOR MEDICAL DEVICES

(75) Inventors: William J. Boyle, Fallbrook, CA (US); Andy E. Denison, Temecula, CA (US); Benjamin C. Huter, Murrieta, CA (US); Scott J. Huter, Temecula, CA (US); John E. Papp, Temecula, CA (US); Charles R. Peterson, Murrieta, CA (US); Kent C. B. Stalker, San Marcos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1927 days.

(21) Appl. No.: 09/897,295

(22) Filed: Jun. 29, 2001

(65) Prior Publication Data

US 2003/0004537 A1 Jan. 2, 2003

(51) Int. Cl.
*A61M 29/00* (2006.01)
(52) U.S. Cl. .................................... 606/192; 604/96.01
(58) Field of Classification Search ................. 606/200, 606/194, 198, 191, 159, 113, 114, 127, 154, 606/192; 604/96.01–109, 264, 523–529; 623/1.1, 1.11
See application file for complete search history.

(56) References Cited

U.S. PATENT DOCUMENTS

| 5,176,659 | A | * | 1/1993 | Mancini ..................... 604/523 |
| 5,766,203 | A | * | 6/1998 | Imran et al. ................. 623/1.11 |
| 5,879,342 | A | * | 3/1999 | Kelley ......................... 600/524 |
| 5,882,347 | A | * | 3/1999 | Mouris-Laan et al. ....... 604/524 |
| 5,944,691 | A | * | 8/1999 | Querns et al. ............... 604/104 |
| 6,039,744 | A | | 3/2000 | Forber |
| 6,123,715 | A | * | 9/2000 | Amplatz ..................... 606/200 |
| 6,171,327 | B1 | * | 1/2001 | Daniel et al. ................ 606/200 |
| 6,221,006 | B1 | * | 4/2001 | Dubrul et al. ............... 600/159 |
| 6,290,710 | B1 | * | 9/2001 | Cryer et al. ................. 606/200 |
| 6,383,206 | B1 | * | 5/2002 | Gillick et al. ............... 606/200 |
| 6,517,765 | B1 | * | 2/2003 | Kelley ......................... 264/510 |

(Continued)

FOREIGN PATENT DOCUMENTS

GB 2 200 848 A 8/1988

(Continued)

*Primary Examiner*—Justine Yu
(74) *Attorney, Agent, or Firm*—Fulwider Patton LLP

(57) ABSTRACT

A deployment control system provides controlled deployment of an embolic protection device which may include a guide wire, an expandable filter attached to the guide wire near its distal end, and a restraining sheath that maintains the expanded filter in a collapsed position. The deployment control system includes a torque control device which allows the physician to torque the guide wire into the patient's anatomy and a mechanism for preventing the guide wire from buckling as the restraining sheath is being retracted to deploy the expandable filter. A recovery control system for recovering the embolic protection device includes an inner catheter which extends within a lumen of an outer recovery sheath in a coaxial arrangement. A distal portion of the inner catheter extends beyond another recovery sheath during advancement of the recovery system into the vasculature. The recovery sheath can be advanced over the inner catheter to collapse the expandable filter. The proximal ends of the inner catheter and recovery sheath include handle portions having snap mechanisms which hold the components together as the recovery system is being advanced into the patient's vasculature.

29 Claims, 11 Drawing Sheets

U.S. PATENT DOCUMENTS

| | | | |
|---|---|---|---|
| 6,544,279 B1 * | 4/2003 | Hopkins et al. | 606/200 |
| 6,616,651 B1 * | 9/2003 | Stevens | 604/524 |
| 6,679,902 B1 * | 1/2004 | Boyle et al. | 606/200 |
| 6,685,722 B1 * | 2/2004 | Rosenbluth et al. | 606/200 |
| 6,887,258 B2 * | 5/2005 | Denison et al. | 606/200 |
| 2002/0058963 A1 * | 5/2002 | Vale et al. | 606/200 |
| 2002/0095170 A1 * | 7/2002 | Krolik et al. | 606/200 |
| 2002/0107541 A1 * | 8/2002 | Vale et al. | 606/200 |
| 2002/0183781 A1 * | 12/2002 | Casey et al. | 606/198 |
| 2004/0044359 A1 * | 3/2004 | Renati et al. | 606/200 |

FOREIGN PATENT DOCUMENTS

| | | |
|---|---|---|
| WO | WO 98/39053 | 9/1998 |

* cited by examiner

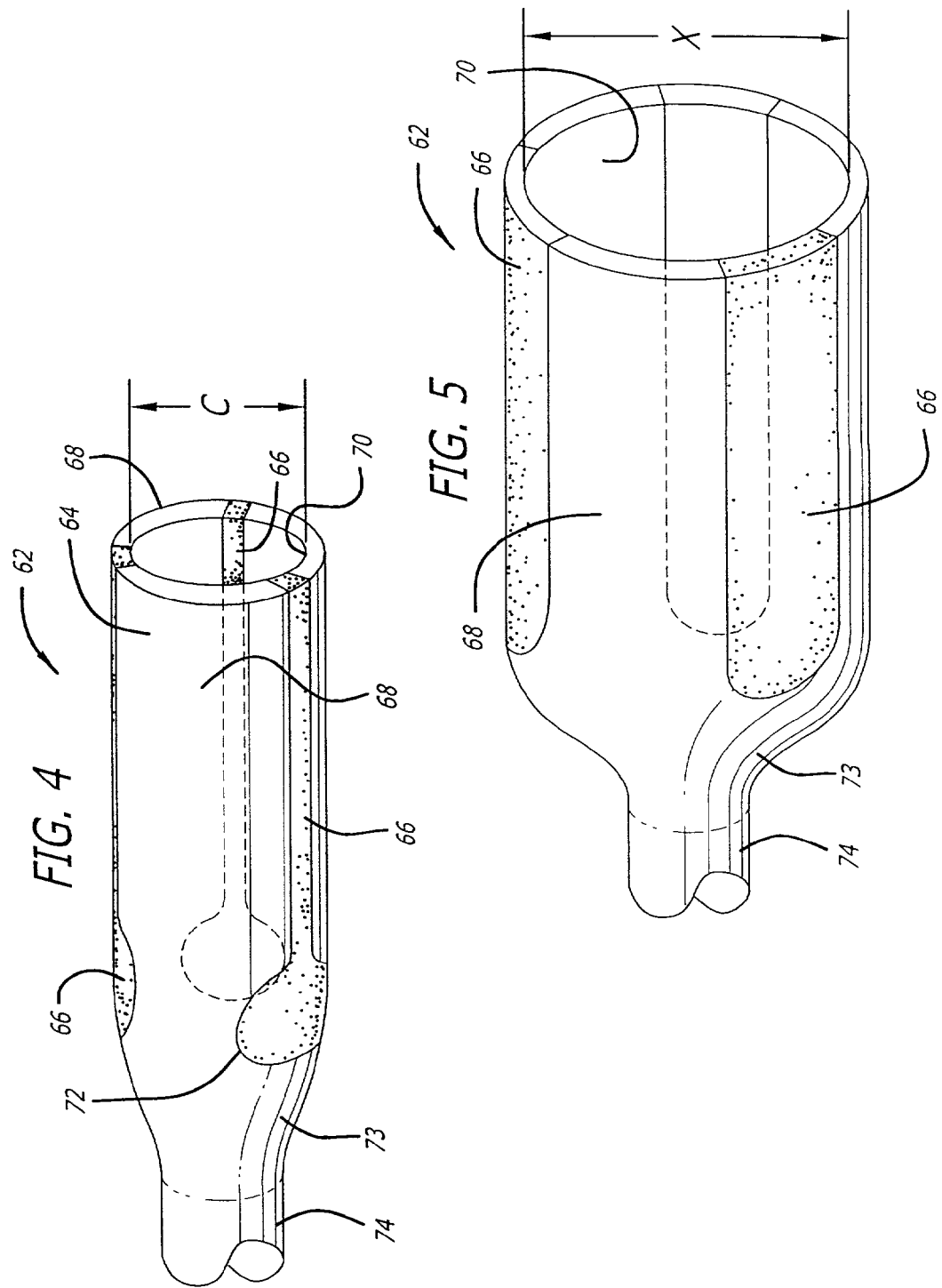

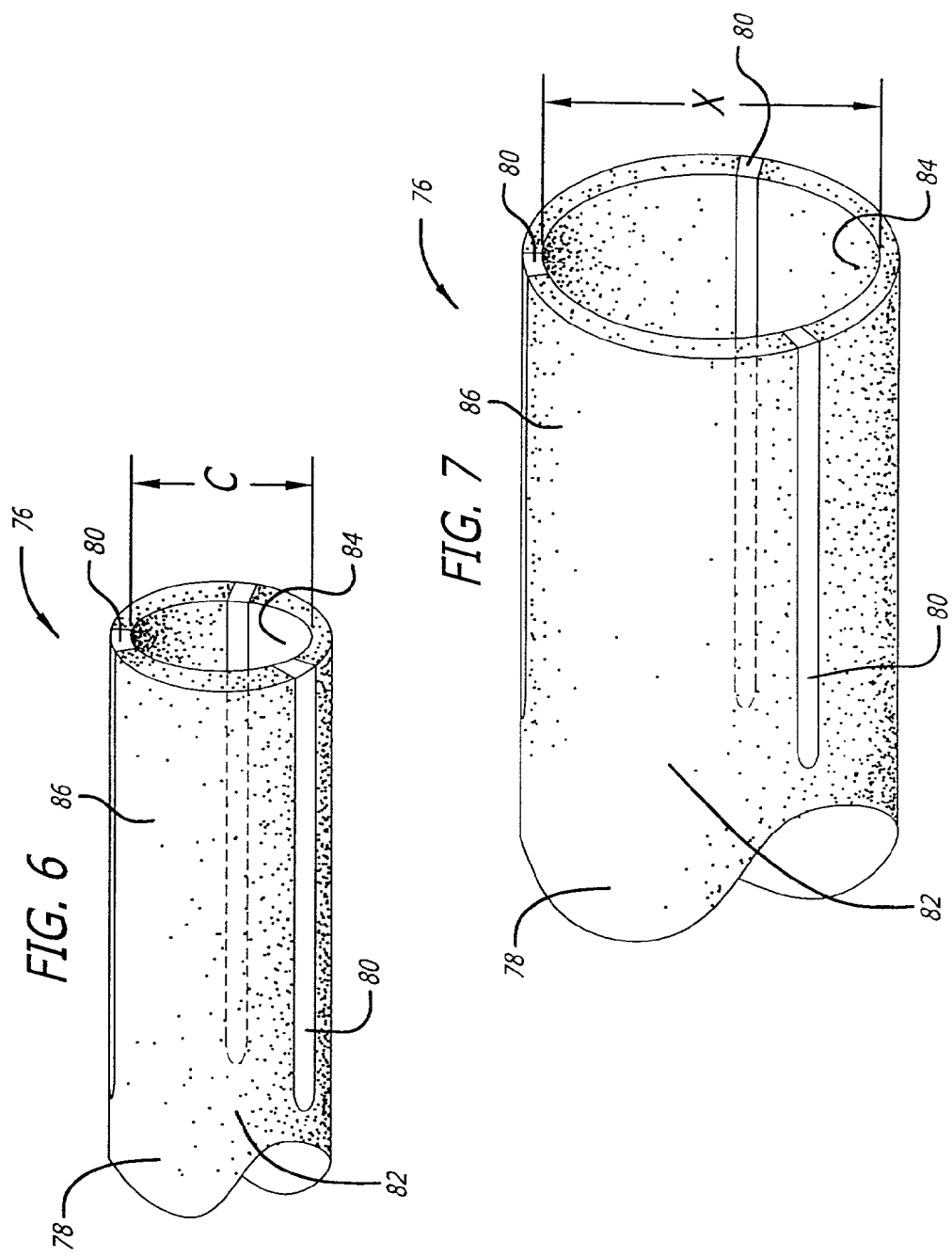

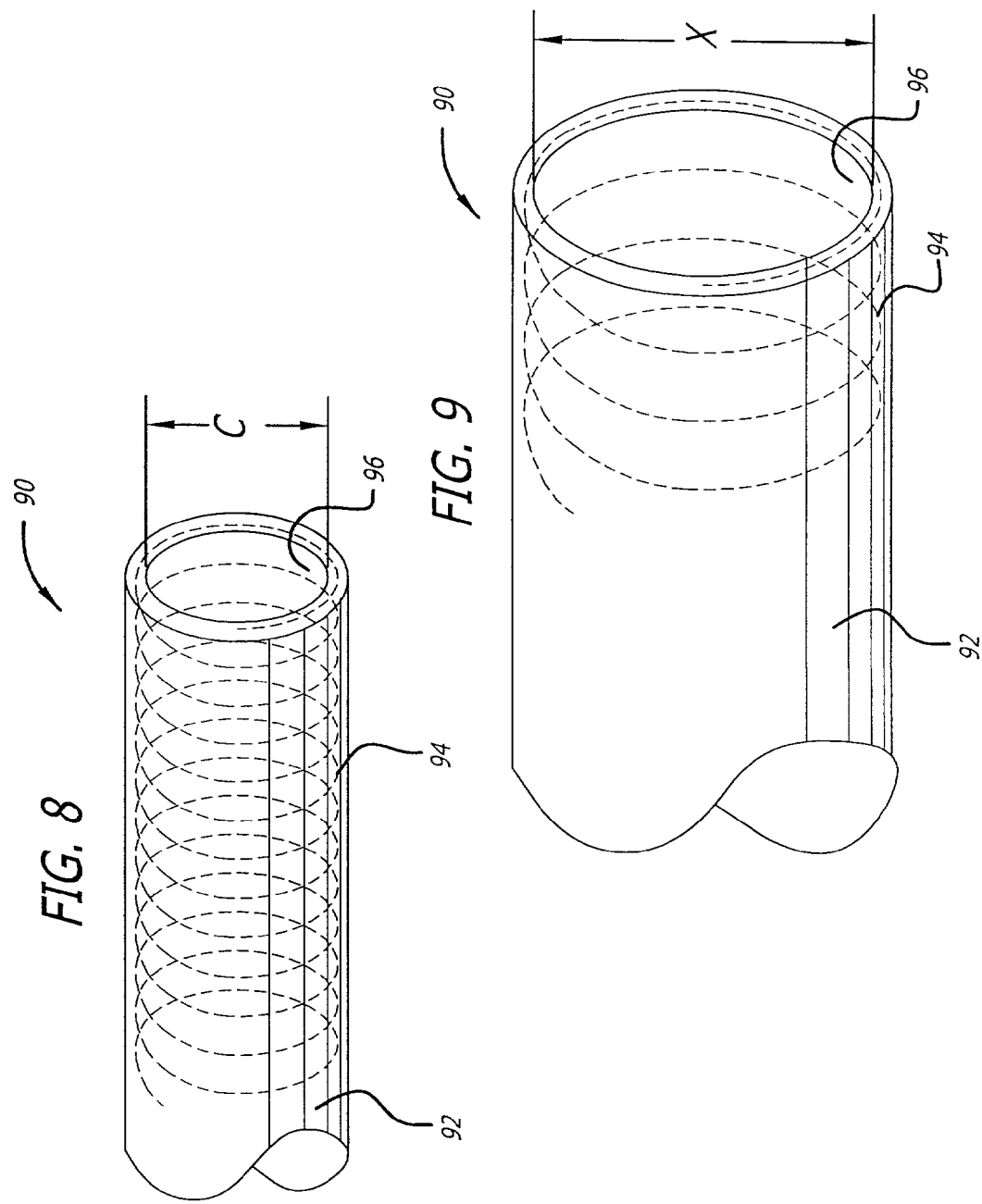

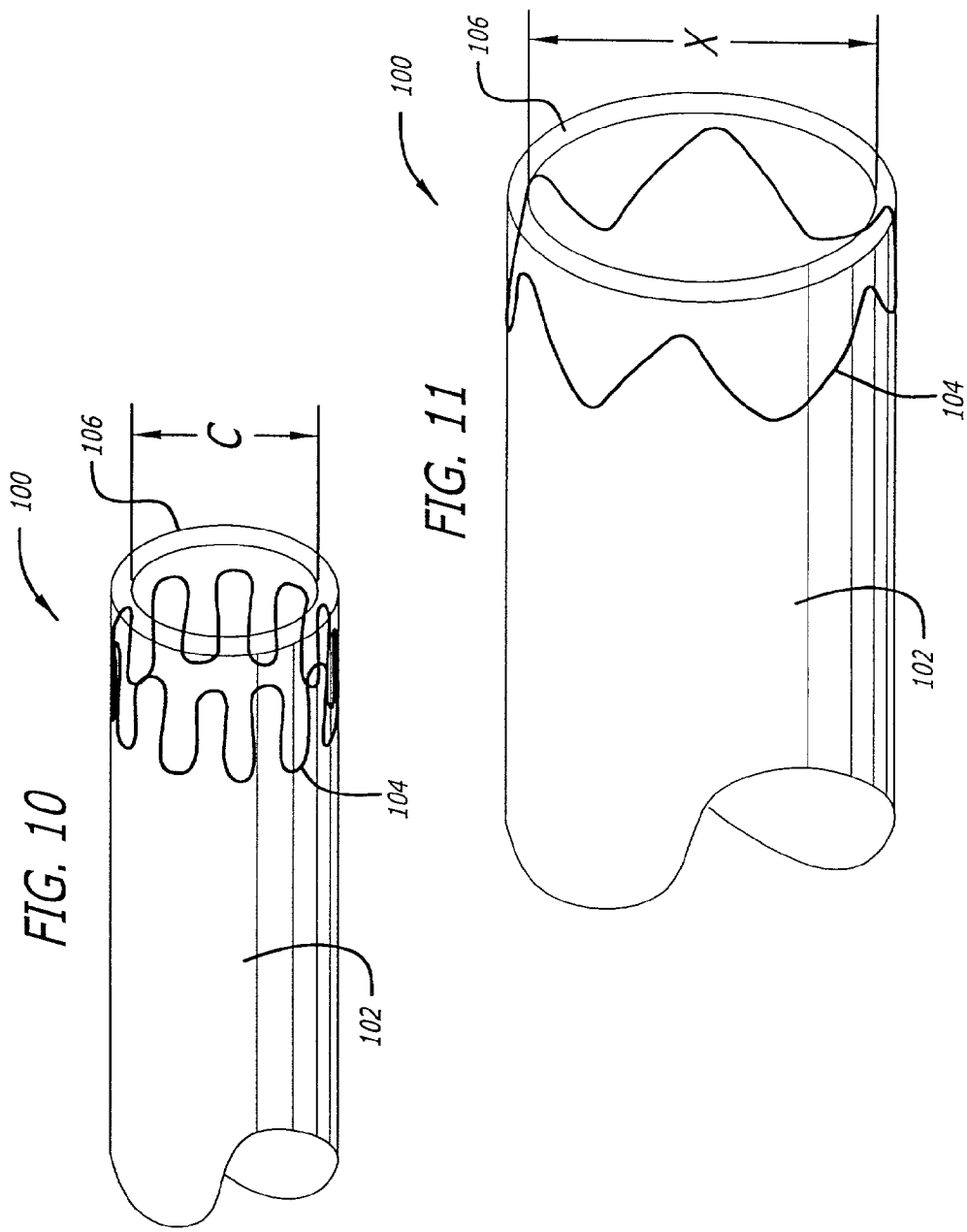

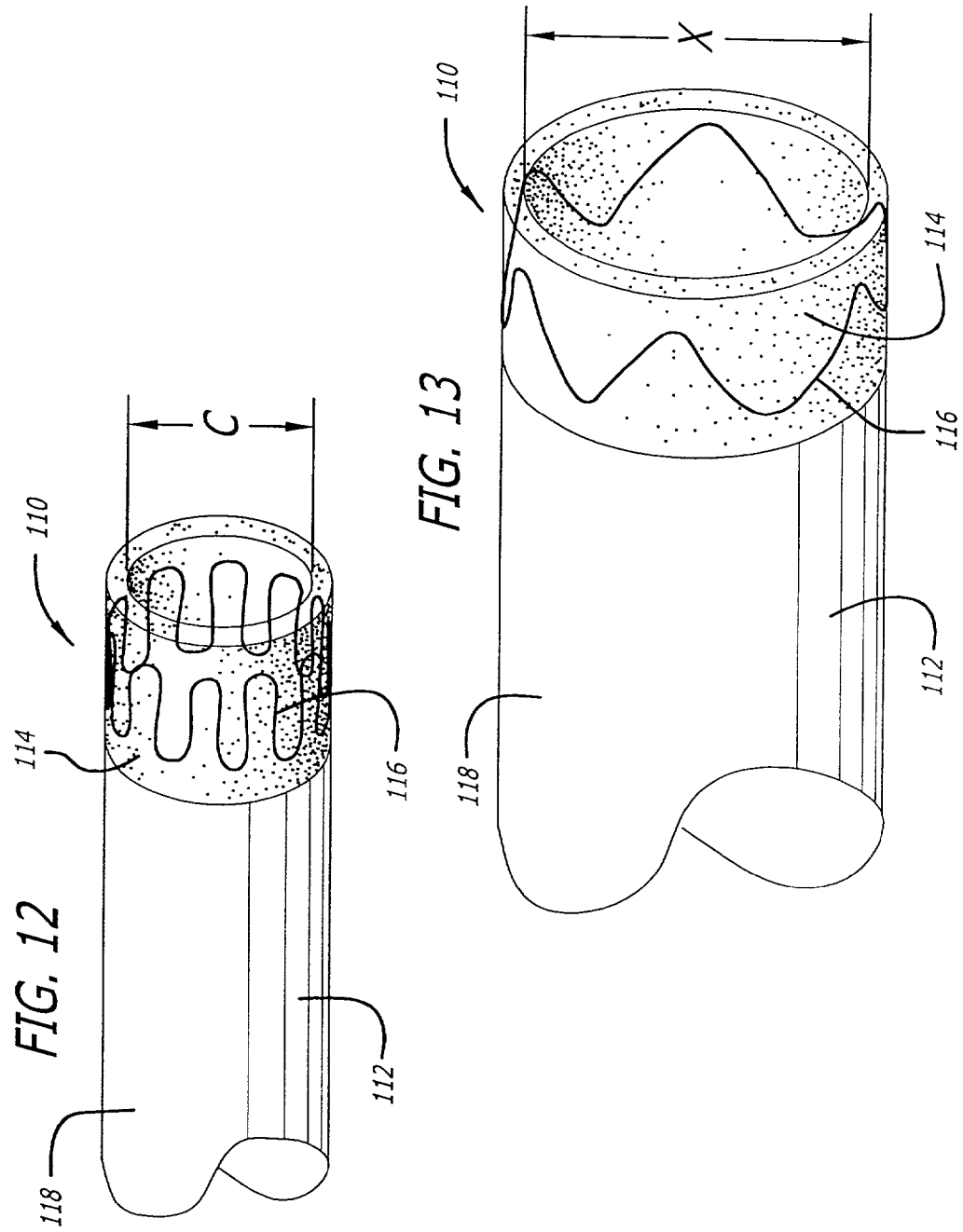

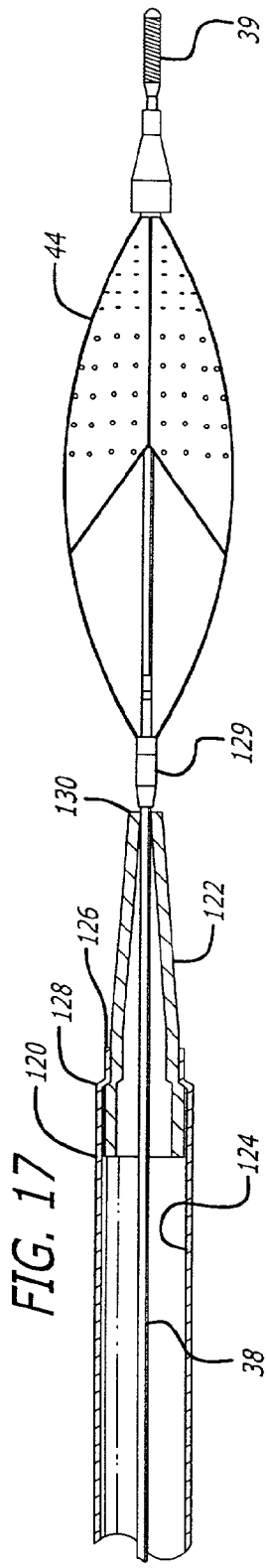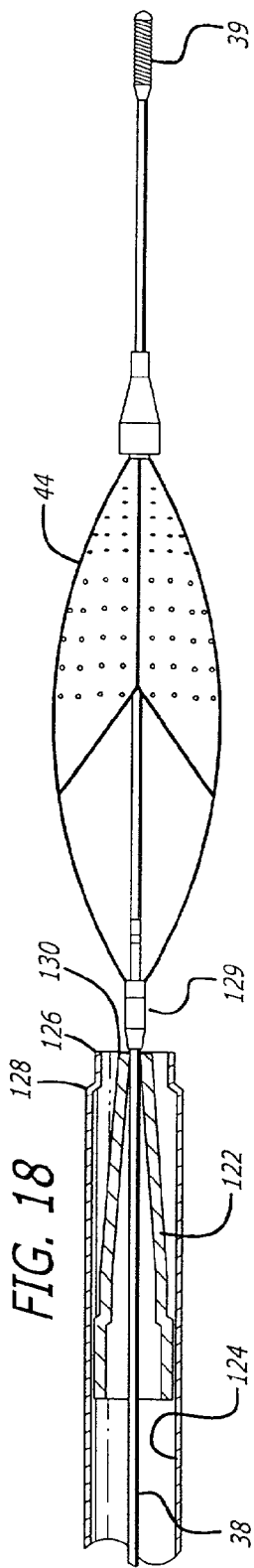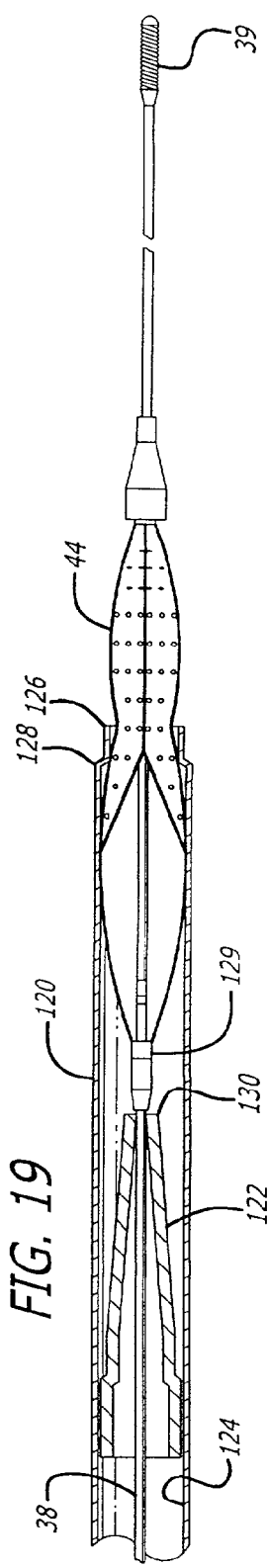

DELIVERY AND RECOVERY SHEATHS FOR MEDICAL DEVICES

BACKGROUND OF THE INVENTION

The present invention relates generally to delivery and recovery devices for use in conjunction with specialized medical devices, such as embolic filter used when an interventional procedure is being performed in a stenosed or occluded region of a body vessel to capture embolic material that may be created and released into the vessel during the procedure. The present invention also can be used to deliver other self-expanding medical devices, such as a self-expanding stent, within a patient's vasculature.

Numerous procedures have been developed for treating occluded blood vessels to allow blood to flow without significant obstruction. Such procedures usually involve the percutaneous introduction of an interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the vessel, resulting in increased blood flow. The balloon is then deflated to a small profile so that the dilatation catheter can be withdrawn from the patient's vasculature. Enhanced blood flow should now resume in the dilated artery. As should be appreciated by those skilled in the art, while the above-described procedure is typical, it is not the only method used in angioplasty.

In the procedure of the kind referenced above, abrupt reclosure may occur or restenosis of the artery may develop over time, which may require another angioplasty procedure, a surgical bypass operation, or some other method of repairing or strengthening the injured area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped onto the balloon portion of the catheter and transported in its delivery diameter through the patient's vasculature. At the deployment site, the stent is expanded to a larger diameter, often by inflating the balloon portion of the catheter.

A variety of stent designs have been developed and include self-expanding stents insertable and deliverable through the patient's vasculature in a compressed state for deployment in a body. Unlike balloon expandable stents which rely on an external radial force to expand the stent at the area of treatment, self-expanding stents are made from materials which are self-expanding in order to move between a compressed or collapsed position to an expanded, implanted position. Stent delivery catheters used for implanting self-expanding stents usually include an inner member upon which the compressed or collapsed stent is mounted and an outer restraining sheath placed over the stent to maintain it in its compressed state prior to deployment. When the stent is to be deployed in the body vessel, the outer restraining sheath is retracted in relation to the inner member to uncover the compressed stent, allowing the stent to move into its expanded condition for implantation in the patient.

These non-surgical interventional procedures, when successful, avoid the necessity of major surgical operations. However, there is one common problem associated with these procedures, namely, the potential release of embolic debris into the bloodstream that can occlude distal vasculature and cause significant health problems to the patient. For example, during deployment of a stent, it is possible for the metal struts of the stent to cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Angioplastic procedures which are performed in occluded saphenous vein grafts, implanted as a result of an open heart surgical procedure, pose a particularly difficult problem to the physician since a large amount of embolic debris is usually generated during the angioplasty procedure.

When any of the above-described procedures are performed in the carotid arteries, the release of emboli into the circulatory system can be extremely dangerous and sometimes fatal to the patient. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system during vessel treatment. One technique which has had some limited success include the placement of a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Some prior art expandable filters are attached to the distal end of a guide wire or guide wire-like member that allows the filtering device to be placed in the patient's vasculature. The guide wire allows the physician to steer the filter to a downstream location from the area of treatment. Once the guide wire is in proper position in the vasculature, the embolic filter can be deployed to capture embolic debris. These embolic filtering devices usually utilize a restraining sheath to maintain the expandable filter in its collapsed position. Once the proximal end of the restraining sheath is retracted by the physician, the expandable filter will move into its fully expanded position. The restraining sheath can then be removed from the guide wire allowing the guide wire to be used by the physician to deliver interventional devices, such as a balloon angioplasty catheter or a stent delivery catheter, into the area of treatment. After the interventional procedure is completed, a recovery sheath can be delivered over the guide wire using over-the-wire techniques to collapse the expanded filter (with the trapped embolic debris) for removal from the patient's vasculature. Both the delivery sheath and recovery sheath should be relatively flexible to track over the guide wire and to avoid straightening the body vessel once in place.

While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

When a combination of an expandable filter and guide wire is utilized, it is important that the guide wire be rotatable so that the physician can steer it downstream of the area of treatment using techniques well known in the art. In this regard, the guide wire is usually "torqued" by the physician to point or steer the distal end of the guide wire into the desired body vessel. Often, when a restraining sheath is utilized, it can be difficult to properly turn the composite device to deliver the filter through the tortuous anatomy of the patient. Moreover, during delivery, it is imperative that the restraining sheath remain positioned over the collapsed filter, otherwise the filter could be deployed prematurely in an undesired location in the patient's anatomy. This occurrence can cause trauma to the walls of the patient's vasculature and would require the physician to re-sheath the expanded filter in order to further advance the filter into the desired area.

When a restraining sheath is utilized to deliver or recover an expandable filter in the patient's vasculature, the length of the sheath can sometimes be problematic to the physician as well. For example, when a full-length restraining sheath is used (i.e., a tubular sheath extending from the area of treatment to an area outside of the patient), the guide wire utilized must have an extended length to allow the sheath to be removed and advanced along the guide wire. As a result, additional medical personnel may be required to hold the guide wire in place when the restraining sheath is being removed to allow the interventional devices to be advanced over the guide wire. The same would be true when a full-length recovery sheath is being used to collapse the expanded filter for removal from the patient's vasculature. Moreover, when full-length sheaths are used for other delivery or recovery, more time is usually needed to remove or advance the sheath along the guide wire.

What has been needed are reliable delivery and recovery sheath which can be used with embolic filtering devices that minimize the above-mentioned incidents from ever occurring. These devices should be relatively easy for a physician to use and should provide an effective means for deploying the embolic filtering device into the desired area of the body vessel and retrieving the same device without releasing any captured embolic debris into the body vessel. Moreover, it would be advantageous if sheaths can be advanced and removed from the guide wire in relatively quick fashion. The inventions disclosed herein satisfy these and other needs.

SUMMARY OF THE INVENTION

The present invention provides delivery and recovery sheaths for use with expandable embolic filtering devices and other medical devices which deliver self-expanding components, such as self-expanding stents and vascular grafts, for implantation in a patient's vasculature. The present invention can be used with an embolic filtering device that generally includes a guide wire having a distal end, a self-expanding filter basket attached to the guide wire near its distal end, and a restraining sheath that maintains the self-expanding filter basket in a collapsed position until it is ready to be deployed in the patient. The present invention eliminates the need for a full-length restraining sheath which have been previously used to deploy and retrieve the filter basket. The present invention provides the physician with a rapid exchange delivery and recovery sheath which can eliminate the need to use long exchange wires when delivering or recovering the expandable filtering device and may reduce the time needed to perform the same. Moreover, the delivery sheath of the present invention can be used not only to deliver the filter to the target location in the patient's anatomy, but can also be used to collapse and retrieve the filtering device once the interventional procedure has been completed. As a result, the present invention eliminates the need for two separate sheaths to be supplied with a single filtering device since one sheath can perform both delivery and recovery functions.

In one aspect of the present invention, the delivery sheath includes an expandable housing portion adapted to collapse and hold the filter basket until the basket is ready to be deployed within the patient. The sheath itself can be attached to a mandrel or guide wire which extends proximally from the sheath. The proximal end of the mandrel extends outside of the patient and is utilized by the physician to manipulate and move the sheath along the guide wire of the filtering device to retract the expandable housing portion from the filter basket. The sheath also includes a lumen which extends from the housing portion and serves as a rapid exchange port for receiving the guide wire of the embolic filtering device. The expandable housing portion of the sheath can be made from a number of different materials and configurations, as will be described herein, to maintain the filter basket in its collapsed position while the filter basket is being advanced or removed from the patient's anatomy.

In one aspect of the present invention, the delivery sheath can be used to deliver a self-expanding stent or vascular graft within the patient's anatomy. In this particular aspect of the invention, the sheath is used with a delivery catheter which includes a member for mounting the stent or graft. Like the filtering device, this delivery catheter is attached to a guide wire or guide wire-like member to allow the physician to steer the self-expanding device into the area of treatment.

In another aspect of the present invention, the expandable housing portion of the sheath is stretchable and elastic to allow the sheath to hold the filter basket in place and prevent premature deployment. In this fashion, the housing portion of the sheath acts to "encapsulate" the filter basket, thus preventing it from being released from the sheath until the physician is ready to do so. Since the sheath is elastic and stretchable, it can achieve a number of different diameters and sizes when recovering or delivering the filtering device. For example, when the present invention is utilized as a recovery sheath, the housing portion will initially contract to its smaller diameter as it tracks along the guide wire of the embolic filtering device. As a result, the possibility that the tip of the sheath could scrape the walls of the body vessel causing a "snow-plow" effect as the device is being advanced over the guide wire is reduced. After the distal tip of the housing portion starts to contact the filter basket, it will begin to expand radially to draw the basket into the housing portion. Once the distal tip starts to expand, the remainder of the sheath begins to expand somewhat allowing the filter basket to be drawn into the remainder of the housing portion. The housing portion has sufficient strength to impart an inward radial force that compresses the filter basket to its smaller diameter permitting the filter device to be subsequently removed from the patient. Once the basket is drawn into the housing portion of the sheath, it will be "encapsulated" to prevent emboli trapped in the filter basket from "back washing" into the body vessel, thus preventing the re-release of potentially damaging emboli into the patient's vasculature .

The expandable housing portion of the sheath can be made in a number of different ways. In one aspect of the present invention, the sheath portion of the device is made from a highly elastic material with a distal tip that expands to collapse the filter basket. An expandable and retractable member, such as self-expanding nitinol wire made from a material such as nickel-titanium (NiTi) would be embedded within the elastic tip material. The wire would be biased to normally contract, but would be radially expandable when subjected to an outward radial force. This would enable the sheath to track closely to the guide wire of the embolic filtering device while still being be able to expand radially to collapse the filter basket when the distal tip contacts the struts of the filter basket.

In another aspect of the present invention, the expandable housing portion would be made from a relatively stiff tubular material which has interspersed therein elastic material that creates expansion members or joints that provide the necessary elasticity to allow the housing portion to expand and contract. In this regard, the tubular portion of the housing provides column strength needed to maintain the embolic basket in its collapsed position and to prevent buckling of the sheath as it is advanced along the guide wire. The highly elastic material forming the expansion members can take on numerous shapes and sizes and can be fitted into spaces cut into the tubular member or molded therein. In still another aspect of the present invention, the expandable housing portion could be formed from a tubular member which is highly elastic and includes reinforcing members that provide the column strength needed when advancing the sheath along the guide wire but do not interfere with the radial expansion of the housing.

The present invention is also directed to a recovery sheath having an inner recovery tip which extends out of the distal tip of the recovery sheath and tracks along the guide wire of the embolic filtering device to prevent a "snowplowing" effect from occurring. The inner recovery tip and the outer recovery sheath are positioned such that a frictional fit between the inner recovery tip and outer recovery sheath is created to maintain the inner tip at the distal end of the recovery sheath as the two components are advanced simultaneously along the guide wire. The frictional fit can be enhanced by a frictional mechanism, such as overlapping ribs located on the surfaces of the recovery sheath and inner tip. Once the inner tip comes in contact with the proximal end of the filter basket and a sufficient amount of force is applied to the inner recovery tip, the frictional fit is overcome allowing the inner tip to slide back into the outer recovery sheath. The distal tip of the recovery sheath will now come in contact with the filter basket in order to collapse the basket. As the basket is retracted into the outer recovery sheath, the inner recovery tip continues to slide proximally back into the outer recovery sheath until the entire embolic filter device is completely recovered.

It is to be understood that the present invention is not limited by the embodiments described herein. Other features and advantages of the present invention will become more apparent from the following detailed description of the invention, when taken in conjunction with the accompanying exemplary drawings.

BRIEF DESCRIPTION OF THE DRAWINGS

FIG. 4 is a perspective view of one embodiment of an expandable housing portion of a delivery and recovery sheath embodying features of the present invention in its contracted position.

FIG. 5 is a perspective view of the expandable housing portion of FIG. 4 in an expanded position.

FIG. 6 is a perspective view of another embodiment of an expandable housing portion of a delivery and recovery sheath embodying features of the present invention in its contracted position.

FIG. 7 is a perspective view, partially in cross-section, of the expandable housing shown in FIG. 6 as it is placed in an expanded position.

FIG. 8 is a perspective view of another embodiment of an expandable housing portion of a delivery and recovery sheath embodying features of the present invention in its contracted position.

FIG. 9 is a perspective view of the housing portion of FIG. 8 in an expanded position.

FIG. 10 is a perspective view of another embodiment of an expandable housing portion of a delivery and recovery sheath embodying features of the present invention.

FIG. 11 is a perspective view of the housing portion of FIG. 10 in an expanded position.

FIG. 12 is a perspective view of another embodiment of an expandable housing portion of a delivery and recovery sheath embodying features of the present invention.

FIG. 13 is a perspective view of the housing portion of FIG. 12 in an expanded position.

FIG. 17 is a side elevational view of a recovery sheath with an inner recovery tip embodying features of the present invention as it approaches the proximal end of a filter basket of an embolic filtering device.

FIG. 18 is a side elevational view of the outer recovery sheath and inner recovery tip of FIG. 17 as the inner recovery tip retracts back into the outer recovery sheath as the outer recovery sheath is advanced to collapse the filter basket.

FIG. 19 is a side elevational view showing the inner recovery tip retracted further into the outer recovery sheath as the filter basket is retrieved by the outer recovery sheath.

DETAILED DESCRIPTION OF THE PREFERRED EMBODIMENTS

Figure 1:
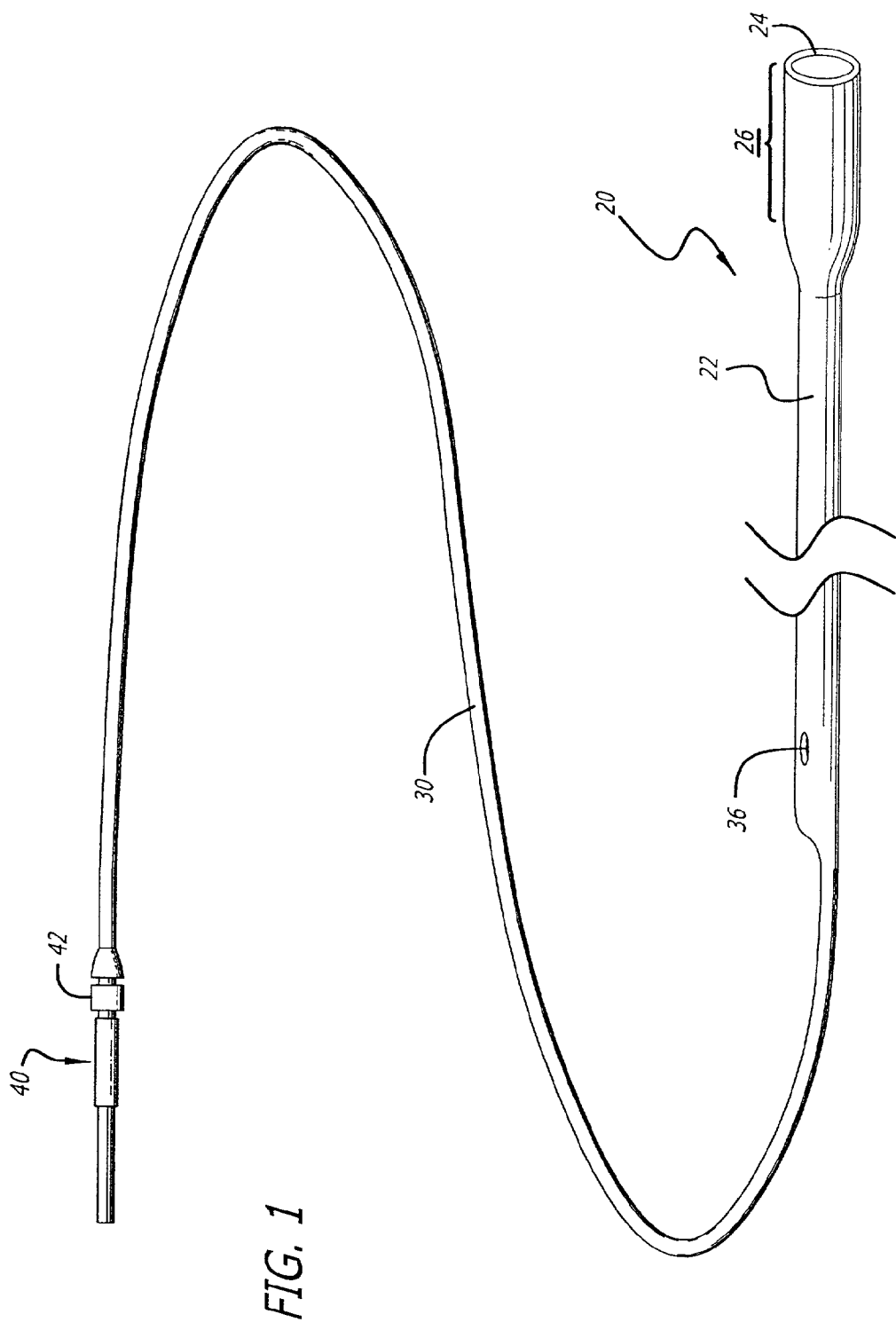
FIG. 1 is a perspective view of a rapid exchange delivery sheath embodying features of the present invention.
Figure 2:
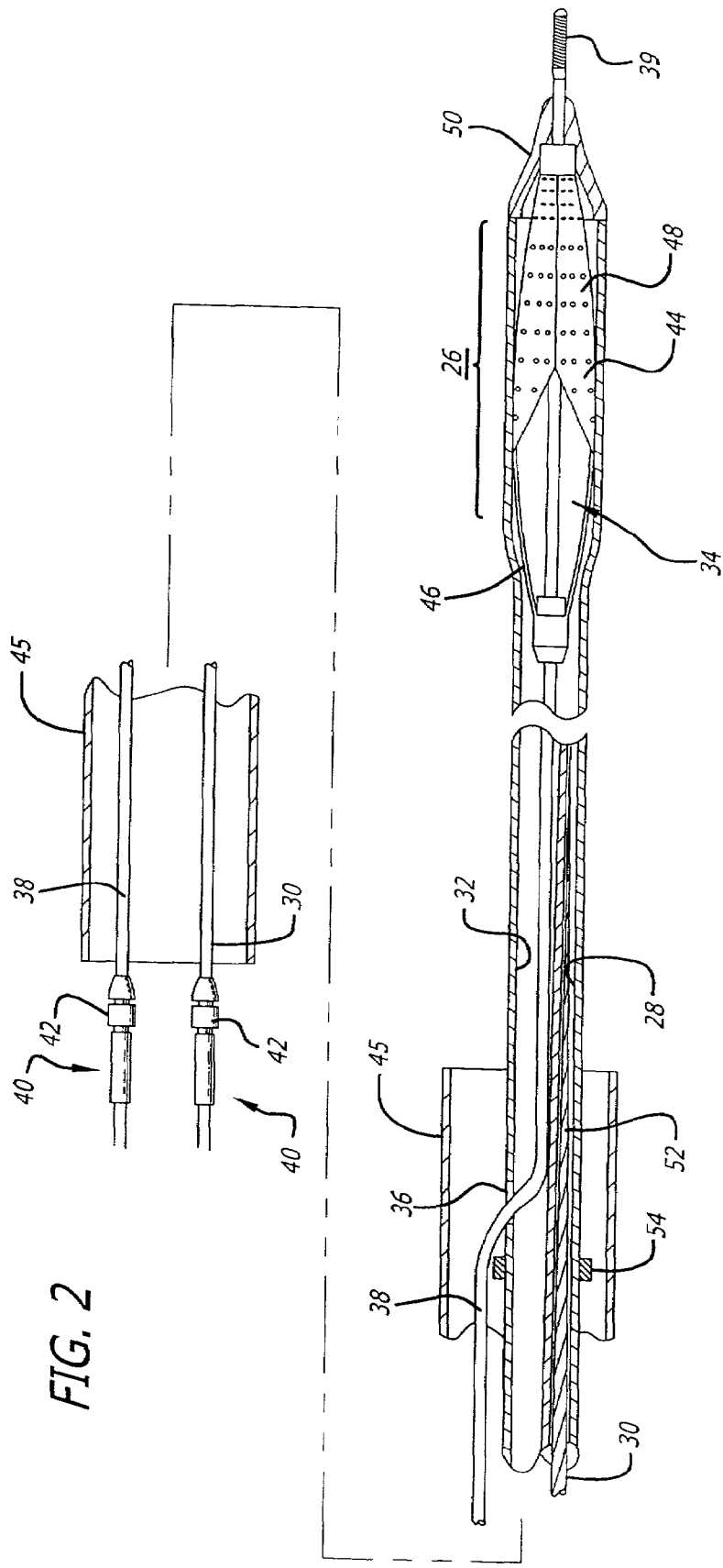
FIG. 2 is an elevational view, partially in cross section, of the distal end of the rapid exchange delivery sheath of FIG. 1, with an embolic filtering device housed therein.

Turning now to the drawings, in which like reference numerals represent like or corresponding elements in the drawings, FIGS. 1 and 2 illustrate a restraining device 20 incorporating features of the present invention. This restraining device is adapted for use with a medical device, such as an expandable embolic filtering device designed to capture embolic debris which may be created and released into a body vessel during an interventional procedure. The restraining device 20 can be used both as a delivery sheath of placing the filtering device into the target area and a recovery sheath for retrieving the device from the patient.

FIGS. 1 and 2 show a particular embodiment of a restraining device 20 incorporating features of the present invention which includes a sheath 22 having a distal tip 24 and expandable housing portion 26. The sheath 22 is a tube-like member which has a lumen 28 extending proximally from the expandable housing portion 26 to receive the distal end of a mandrel 30. The sheath 22 also has a second lumen 32 which extends proximally from the housing portion 26 to form a channel for receiving guide wire 38 of an embolic filter device 34, such as the one shown in FIG. 2. The lumen 32 has an opening 36 through which the guide wire 38 can extend therethrough. The mandrel 30 has a proximal end 40 and a torquing handle 42 which is manipulated by the physician when positioning the restraining device 20 and embolic filtering device 34 in the patient's vasculature.

The embolic filtering device 34, as shown in FIG. 2, includes an expandable filter basket 44 having a plurality of self-expanding struts 46 which are attached to a filtering element 48. The embolic filter device 34 also includes an obturator 50 affixed to the distal end of the filter basket 44 to prevent possible "snowplowing" of the embolic filtering device during delivery to the vasculature. This obturator can be made from a soft polymeric material, such as PEBAX D 40, and has a smooth surface which creates a substantially smooth outer surface when placed adjacent to the sheath 22.

As is shown in FIG. 2, the guide wire 38 of the embolic filtering device 34 extends through the lumen 32 of the sheath 22 and extends proximally outside of the patient. The physician can manipulate the proximal end (not shown) of the guide wire 38 with a torque handle to steer the distal guide wire tip 39 and restraining device 20 into the desired location in the patient's vasculature. It should be appreciated to those skilled in the art that the filter basket 44 should be rotatably affixed to the guide wire 38 to allow the guide wire to be rotated freely as the filter basket 44 is held in place by the housing portion 26 of the sheath 22. As can be further seen in FIG. 2, the mandrel 30 has a tapered distal tip 52 which creates a bit more flexibility to the device near its distal end where flexibility is required when the physician steers through the sometimes tortuous anatomy of the patient. A marker band 54 located proximal to the opening 36 of the rapid exchange lumen 32 would be used both as a marker to help the physician in locating the device when using fluoroscopic instruments and would also be able to keep the opening 36 inside the guiding catheter or sheath 45 at all times. This helps to prevent these components from damaging the system. Additionally, the mandrel can be coated with a polymeric coating, or PTFE (Teflon®) in order to provide a lubricious coating which helps when advancing the device through the guide catheter (not shown).

The overall length of the restraining device 20 would be approximately 75 to 190 centimeters. The overall length of the device will depend, of course, upon the type of medical component being delivered by restraining device 20, along with the location of the intended area of treatment and the area of access. These figures can change accordingly. The sheath 22 would be approximately 70 to 185 centimeters in length with the expandable housing portion 26 being approximately 3 centimeters in length in order to properly hold the embolic filtering device 34. It should be appreciated that the size of the expandable housing portion 26 can vary in accordance with the size and length of the self-expanding medical component which it is restraining. For example, as would be shown below, different medical devices can be used in conjunction with the present invention which may have a larger or smaller overall length that would change the size needed for the housing portion 26. The majority of the sheath 22 is dedicated to the lumen 28 which holds the mandrel and the rapid exchange lumen 32 that receives the guide wire of the embolic filtering device. It should be appreciated that this length can also vary depending upon any given application, although other lengths are particularly suited since the sheath 22 is intended to extend out of the guide catheter (see FIGS. 2 and 3) while the mandrel 30 is usually housed within the sheath 22 itself. It should be noted that although a mandrel 30 is shown, this particular elongated member can be any one of a number of different structures including a guide wire or other guide wire-like devices.

Figure 3:
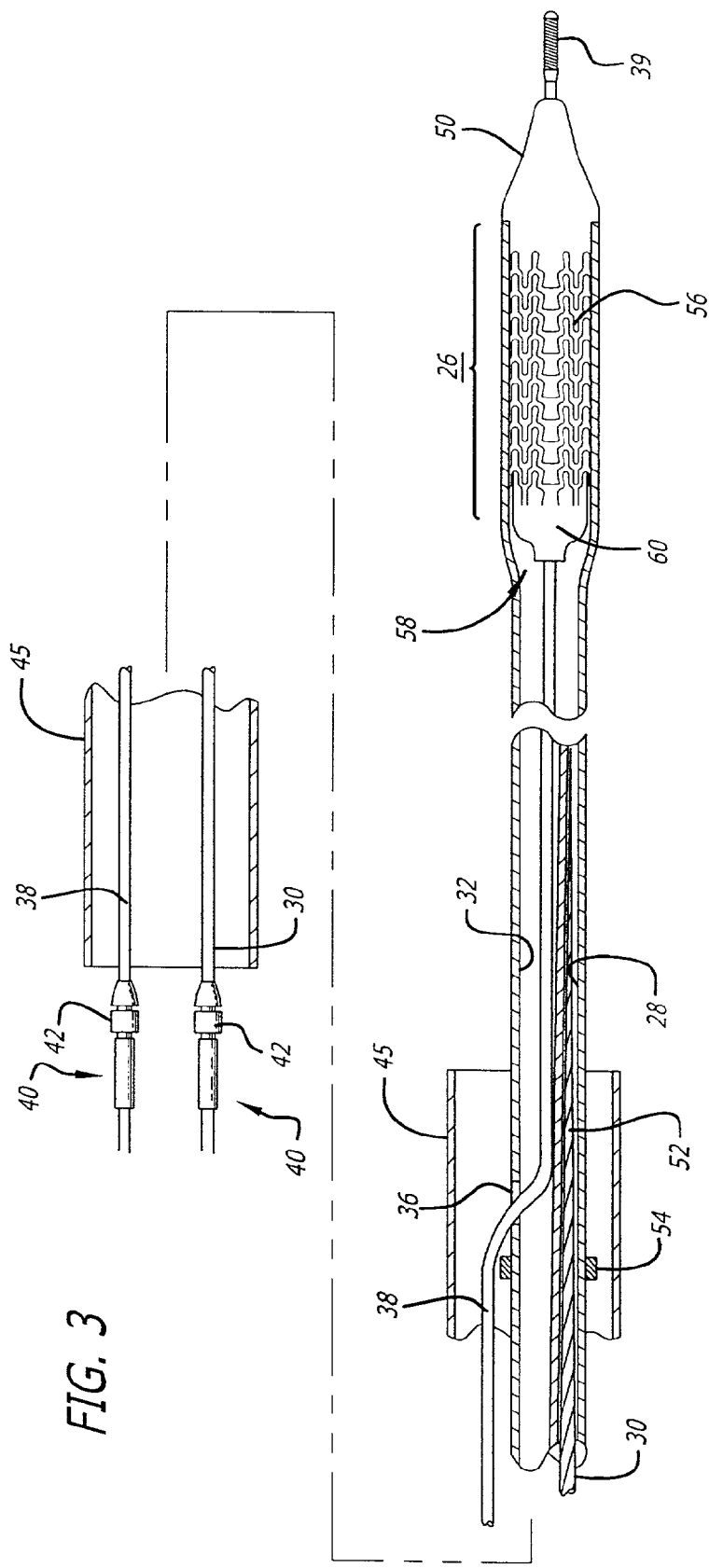
FIG. 3 is an elevational view, partially in cross section, of the distal end of the rapid exchange delivery sheath of FIG. 1, with a self-expanding stent housed therein.

Referring now to FIG. 3, the versatility of the present invention is shown as the restraining device 20 is utilized in delivering a self-expanding medical component, namely a stent 56, within the patient's vasculature. In this particular figure, the stent 56 is mounted onto a delivery device 58 that includes a mounting region 60 upon which the collapsed stent is placed during delivery. The delivery device 58 also includes a guide wire 38 which extends from the mounting region 60 to provide the physician with an end that can be manipulated to steer the device into the area of treatment. This particular delivery device may also include a obturator 50 which also forms a smooth transition surface to the outer surface with the sheath 22 to prevent possible "snowplowing" when the device is being steered through the patient's vasculature. It should be appreciated that the delivery device 58 depicted herein is just one example of numerous different delivery devices which can be utilized in accordance with the present invention. Generally, the delivery device 58 includes a mounting region and a steerable guide wire which allows the physician to manipulate the device into the target area. Additionally, while a stent is shown on this particular delivery device, it also possible to mount another medical device, such as a vascular graft having self-expanding rings which can be deployed within a patient's vasculature as well. In such a case, the mounting region may be longer in length to accommodate the vascular graft. Likewise, the housing portion 26 of the sheath 22 may have to be longer in length to accommodate the larger medical component. Again, the size, shape and length of the restraining device 20 can be varied in order to accommodate the particular medical component that it is delivering to the target location.

In use, the embolic filtering device 34 would be delivered within a body vessel of the patient, such as an artery. The filter basket 44 would be placed downstream from an area of treatment where an interventional procedure is to be performed. In this manner, the area of treatment might be an artherosclerotic stenosis in which plaque has built up against the inside wall of the artery. The therapeutic interventional procedure may comprise the implantation of a stent to increase the diameter of the occluded artery and increase the blood flow therethrough. It should be appreciated that the embodiments of the present invention are illustrated and described herein by way of example only and not by way of limitation. Also, those skilled in the art will appreciate that the present invention can be used in other body vessels, such as the coronary arteries, carotid arteries, renal arteries, saphenous veins and other peripheral arteries. Additionally, the present invention can be utilized to deploy an embolic filtering device when a physician performs any one of a number of interventional procedures, such as balloon angioplasty, laser angioplasty or atherectomy, which requires the need for a filtering device to be located downstream from the area of treatment.

Referring now to FIGS. 4 and 5, an expandable housing portion 62 incorporating features of the present invention is shown. In this particular embodiment, the sheath 64 is made from two different materials which provide the elasticity and flexibility needed to preform the functions of the recovery sheath. As is shown in FIGS. 4 and 5, the sheath 64 includes highly elastic expansion members 66 which are interspaced between sections 68 of low expansive material that provides column strength and axial stiffness to the housing portion 62. The expansion members 66 extend lengthwise across the housing portion 62 and function in such a manner as to provide elasticity to cause the normal diameter C of the housing portion 62 (FIG. 4) to expand to the larger diameter X as shown in FIG. 5. The low expansion section 68 can be made from, for example, a soft material loaded with radiopaque materials to provide additional radiopacity to the sheath 64. For example, the material for the section 68 could be PEBAX 40 D loaded with known radiopaque materials. Other suitable materials include polymeric materials such as cross-linked HDPE, polyolefin and polyamide. The expansive members 66 could be highly elastic materials which include biocompatible polyurethane, silicone, polyisoprene and lower durometer PEBAX.

As can be seen in FIG. 5, once an outer expansive force is placed on the inside surface 70 of the housing portion 62, the expansion member 66 will expand causing an increase in the inner diameter as is shown. The low expansion sections 68 remain relatively unchanged although it should be appreciated that some expansion could possibly take place depending upon the materials which are utilized for this particular portion of the housing 62. Although the particular embodiment shown in FIGS. 4 and 5 utilize three expansion members 66 which extend longitudinally along the length of the housing portion 62, it should be appreciated that the number of expansion members which is utilized can vary depending upon the particular properties which are to be achieved. For example, more or less expansion members can be utilized as needed. Additionally, the elasticity of the material used for the expansion members could also dictate the number, size and location of expansion members which can be interspersed onto the housing portion 62. Additionally, although the expansion members are shown substantially as longitudinal strips which extend longitudinally along the housing, a variety of different shapes and sizes could be utilized without departing from the spirit and scope of the present invention. Additionally, each end of the expansive member 66 can include a circular shape 72 which allows the low expansion sections 68 to expand without tearing.

As is shown in FIGS. 4 and 5, this particular sheath 64 includes a proximal end 73 which tapers to a tubular member 74 that extends proximally to an outside location from the patient. In this manner, the expandable housing portion 62 can be part of a elongated tubular member which creates a full-length sheath. In this manner, the tubular member 74 would have an internal lumen formed therein which receives the guide wire of the medical device, such as the embolic filtering device, which would be restrained within the housing portion 62. Alternatively, the sheath 64 could be made with two lumens forming a rapid exchange lumen and a lumen for receiving a mandrel to create the rapid exchange-type restraining device as shown in FIGS. 1-3.

Referring now to FIGS. 6 and 7, another embodiment of the expandable housing portion 76 of a sheath 78 is shown. In this particular embodiment, the sheath 78 includes reinforcing members 80 disposed within a tubular member 82, made from highly elastic material. This highly elastic tubular member 82 is adapted to expand up and over the filter basket as has been described herein and is shown in greater detail in FIGS. 14-16. In this particular embodiment, the sheath 78 is primarily formed from the elastic tubular member 82 with the reinforcing members 80 being disposed to provide column strength to the housing portion 76. As is shown in FIG. 7, the elastic tubular portion 82 is expandable to a larger diameter X to extend over the filter basket when the device is to be retrieved from the patient's vasculature. The reinforcing members 80, as shown in FIG. 7, do not expand with the tubular portion 82 but provide reinforcing characteristics to prevent the housing portion 78 from buckling as it is being advanced along a guide wire. These reinforcing members 80 are disposed along the tubular member 82 such that they will not interfere with the radial expansion of the tubular member 82. The reinforcing member can be loaded with a material having high radiopacity to increase the ability to visualize the sheath within the patient using a fluoroscope, or other visualization equipment.

The particular embodiment shown in FIGS. 4 and 5 can be made by selecting a cylindrical or tubular member made from a low elastic material, such as the PEBAX 40 D, as described above. Slots which correspond to the size, shape and location of the expandable expansion members 66 can then be cut into the tubular member creating voids into which the material forming the expansion members 66 can be placed. For example, slots could be cut into the material by a laser or by mechanical means. A coated mandrel could then be inserted into the inner diameter of the tubular member to provide rigidity to the sheath as the expansion members are being formed. The highly elastic material to be used for the expansion member 66 could then be dissolved in volatile solution which would be applied at the cut or lased areas to create the highly elastic expansion members. The elastic material can then cure within the cut or lased pattern to create the expansion members 66. While this is just one method for manufacturing this sheath, it should be appreciated that the expansion members could be cut from an elastic material and physically bonded within the slots formed on the tubular member, as well. Still other ways of manufacturing the composite unit can be utilized.

In a similar fashion, the housing portion 78 of the sheath 78 shown in FIGS. 6 and 7 could be made in much the same way. A tubular member having high elasticity can be selected and stiffer reinforcing members 80 can be physically applied to the member. For example, slots can be cut into the member with reinforcing members 80 bonded or otherwise affixed within the slots to form a composite unit. It should be appreciated that although the reinforcing members 80 are shown as being embedded into the tubular member 82, they could also be formed from thinner strips which are applied to the inner surface 84 or outer surface 86 of the sheath 76. Again, the number, location and size of the reinforcing members 80 can vary depending upon the application and the particular materials which are being utilized to create the sheath 78. This particular sheath 78 can be incorporated into a rapid exchange-type sheath as shown in FIGS. 1-3, or alternatively, could be incorporated into a full-length sheath as shown in the design of FIGS. 4 and 5. The materials which can be utilized for the reinforcing members include stainless steel, polymers and nickel-titanium alloys such as nitinol.

Referring now to FIGS. 8 and 10, an alternative embodiment of an expandable housing portion 90 incorporating features of the present invention is shown. In this particular embodiment, the sheath 92 includes a coil spring 94 embedded into the sheath 92 to provide the elasticity needed to expand the housing portion 90 when needed. In this embodiment, the coil spring 94 can be permanently set into the material forming the sheath 92 or it could be attached to the outside or inside surface of the sheath as well. In use, the coil spring 94 is normally biased to the smaller collapsed diameter C, as shown in FIG. 8. Thereafter, when a outward radial force is applied to the inner surface 96 of the housing portion 90, the coil spring expands outwardly allowing the housing portion to expand as needed to capture the filter basket. The coil spring 94 can be made from a material such as nickel titanium, spring steel or a plastic material having high flexibility. The sheath 92 can be made from a soft material with high elongation or elasticity, such as silicone, polyurethane or other stretchable material.

FIGS. 10 and 11, show another embodiment of the expandable housing portion 100 is shown as it is affixed to a sheath 102. In this particular embodiment, an expandable ring member 104 is utilized near the distal end 106 of the housing portion 100. This particular ring member can be made from material such as nickel titanium or spring steel. As can be seen in FIGS. 10 and 11, the ring member 104 has undulations which allow the ring member to expand radially outward as shown in FIG. 11 to increase the diameter of the housing portion 100. The ring member 104 is normally biased to the collapsed diameter C, as shown in FIG. 10. The ring member 104 can be either attached to the outside surface or inside surface of the sheath 102 or can be formed directly into the sheath 102 using molds and other known techniques well-known in the art. Again, the sheath 102 should be made from an elastic material such as silicone, polyurethane or other highly stretchable material.

Referring now to FIGS. 12 and 13, yet another example of an expandable housing portion 110 of a sheath 112 is shown. In this particular embodiment, the housing portion 110 includes a distal tip portion 114 which includes a ring member 116, similar to the one shown in FIGS. 10 and 11. In this particular embodiment, the distal tip portion 114 can be made from a material which is different from the remaining portion of the sheath 112. For example, the tip material can be made from a material which is even more elastic than the portion 118 which forms the remainder of the sheath 112. In this regard, the tip of the sheath will be highly elastic yet will have a biasing member which contracts the tip once the tip extends over the component to be restrained, such as the filter basket of an embolic filtering device. The tip portion 114 can be adhesively bonded to the remaining portion 118 of the sheath 112 using adhesives, or other bonding or molding techniques. Again, the ring member 116 can be either embedded into the material forming the tip portion 114 itself, or can be applied to the outer surface or inner surface of this portion of the sheath as well.

Figure 14:
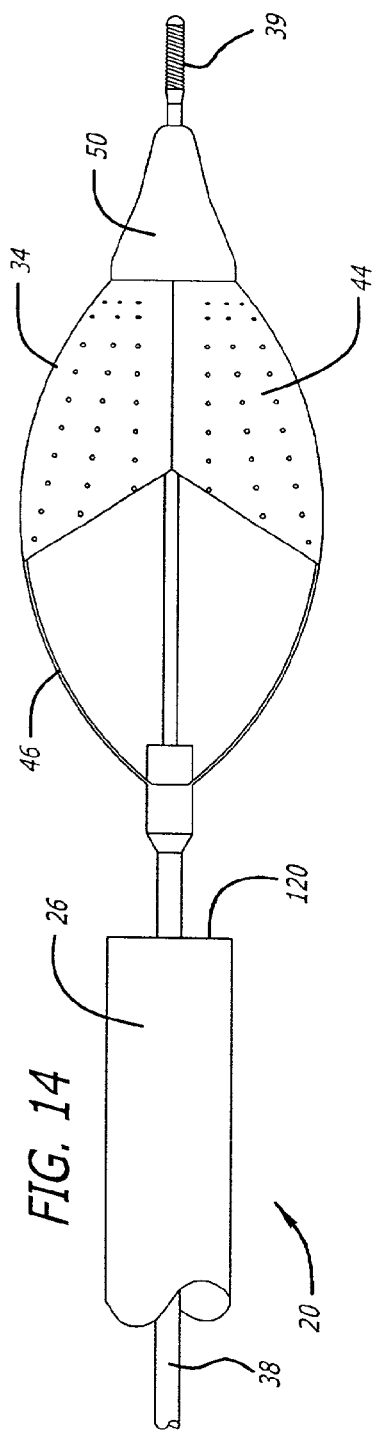
FIG. 14 is a side elevational view showing an expandable housing portion made in accordance with the present invention as it approaches an expandable filter basket for recovery purposes.
Figure 15:
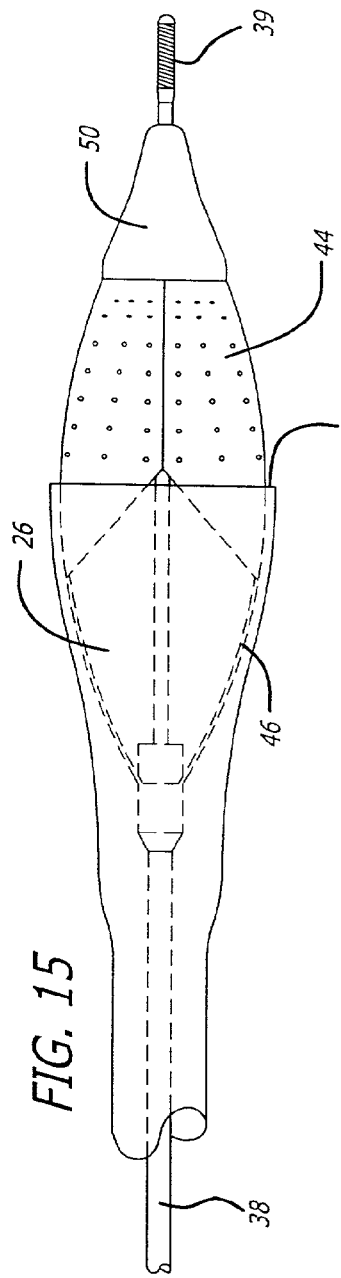
FIG. 15 is a side elevational view of the expandable housing portion of FIG. 14 as it begins to collapse the filter basket of the embolic filtering device.
Figure 16:
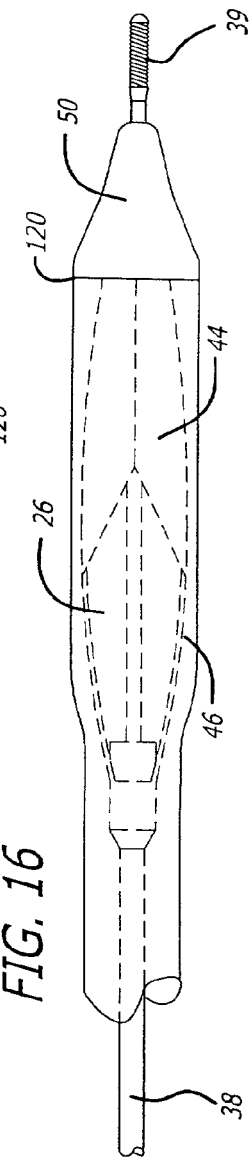
FIG. 16 is a side elevational view of the expandable housing portion of FIG. 14 as it completely recovers the filter basket of the embolic filtering device.

FIGS. 14-16, show the use of a restraining device 20 which incorporates the features of the present invention is shown as it is retrieving an embolic filtering device 34, similar to the one shown in FIG. 2. Referring first to FIG. 14, the expandable housing portion 26 is shown as it is approaching the proximal end of the filtering device 34. The distal tip 120 of this expandable housing portion 26 is shown conforming close to the diameter of the guide wire to closely track to the guide wire as it is being advanced into the patient's vasculature, thus avoiding a possible "snowplowing" effect on the vascular walls of the patient. As the distal tip 120 of the expandable housing portion 26 contacts the struts 46 of the filter basket 44, it begins to expand somewhat since the outward radial force being produced by the expanded filter basket is greater than the contracting force. As is shown in FIG. 16, as the distal tip 120 extends over the filter basket 44 and contacts the obturator 50, the collapsing forces of the housing portion 26 take over to collapse the filter basket back to its collapsed position. In this fashion, the filter basket 44 is fully encapsulating to prevent any embolic debris that which may have been collected in the filter element 16 from backflowing into the body lumen. As a result, the housing portion 26 encapsulates the filter basket for removal from the patient without the fear of releasing captured embolic material. This particular sequence is typical of the manner in which all of the embodiments disclosed and described herein would functions during usage. This is irregardless of whether the housing portion is formed as a rapid exchange-type sheath or is incorporated into a full-length sheath.

Referring now to FIGS. 17-21, another embodiment of a recovery sheath 120 made in accordance with the present invention is shown. As is seen in FIG. 17, the recovery sheath 120 includes an inner recovery tip 122 located within the recovery sheath 120. This recovery sheath 120 has a lumen 124 through which a guide wire 38 extends. The recovery sheath 120 and inner recovery tip 122 are designed to collapse and retrieve a device, such as an embolic filter device, as shown in FIGS. 17-19. The recovery sheath 120 includes a tip portion 126 designed to come in contact with a shoulder portion 128 formed on the recovery tip 122. In this manner, the recovery tip 122 will not be removable past the distal tip 126 of the recovery sheath. The recovery tip 122 and recovery sheath 120 are in frictional contact with each other and will remain in contact until a sufficient external force is applied to the recovery tip to causes it to slide back into the lumen 124 of the recovery sheath 120. As is shown in FIG. 18, this inner recovery tip 122 retracts back into the recovery sheath 120 when an external force is placed at the distal end 130 of the inner tip 122. As the recovery tip 122 contacts the proximal fitting 129 of the filter basket 44, a sufficient force will cause the recovery tip 122 to retract back inside of the restraining sheath 120. Thereafter, as shown in FIG. 19, as an additional force is used to retract the filter basket 44 back into the recovery sheath 120, the recovery tip 122 will retract even further back into the sheath to allow the filter basket to be retrieved for removal from the patient. In this manner, the recovery tip 122 permits the recovery sheath 120 to be advanced along the guide wire to patient's vasculature without causing a "snowplowing" effect. Thereafter, once the recovery tip reaches the filter basket, it can be retracted backwards into the sheath to allow for the recovery of the filter basket.

Figure 20:
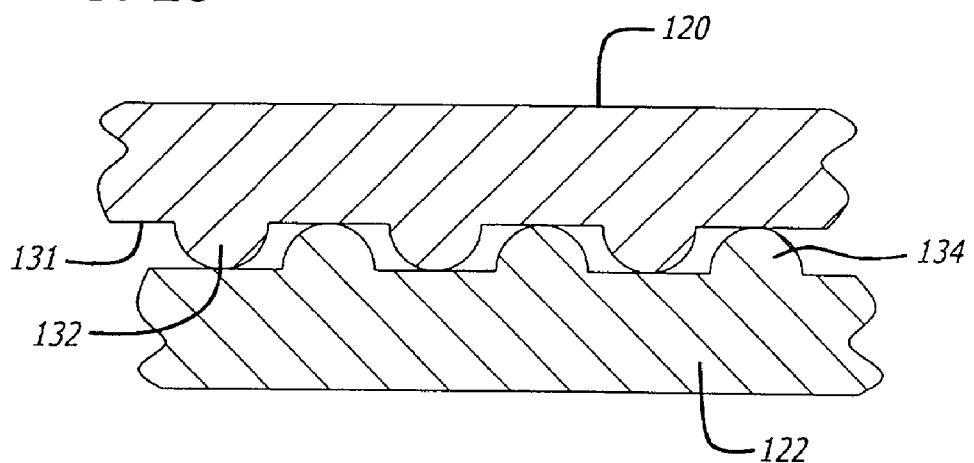
FIG. 20 is a side elevational view, in cross-section, showing the frictional mechanism which enhances the frictional contact between the recovery sheath and inner recovery tip shown in FIG. 17.
Figure 21:
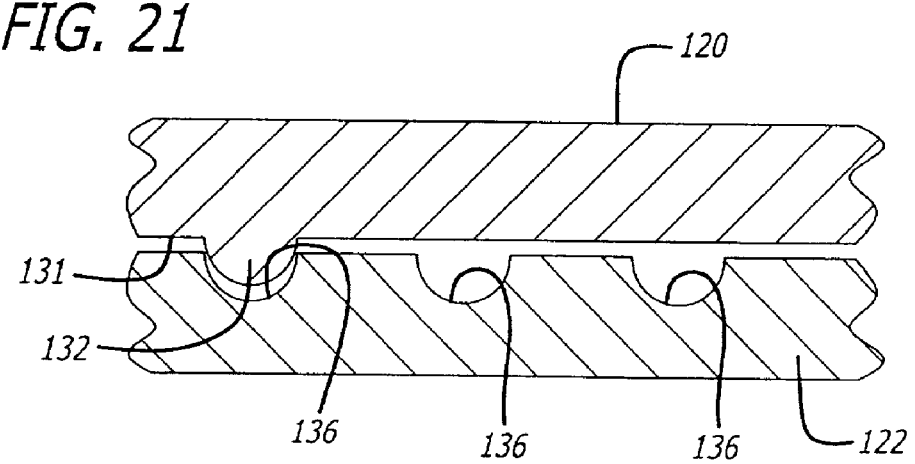
FIG. 21 is a side elevational view, in cross-section, of another embodiment of a frictional mechanism which enhances the frictional contact between the outer recovery sheath and inner recovery tip of FIG. 17.

Referring now specifically to FIGS. 20 and 21, the frictional fit which is created between the inner recovery tip 122 and recovery sheath 120 can be enhanced by a mechanism for increasing the frictional force between these two components. As can be seen in FIG. 20, the surface 131 of the restraining sheath 120 includes a number of outwardly projecting ribs 132 which are formed within the lumen 124. The inner recovery tip 122 likewise includes a number of outwardly projecting ribs 134 designed to be placed between the ribs 132 of the recovery sheath 120. In this manner, the two sets of ribs 132 and 134 intermesh to help increase the frictional force between the recovery sheath 120 and the inner recovery tip 122. When a sufficient amount of axial force is applied to the inner recovery tip 122, as is shown in FIG. 18, the interconnection between the sets of ribs will be end, allowing the inner recovery tip 122 to slide back within the lumen 124 of the recovery sheath 120. This is just one example of simple mechanism which can be utilized to increase the frictional contact between these two members.

Referring now specifically to FIG. 21, an alternative frictional mechanism is illustrated. In this particular figure, the recovery sheath 120 includes a single rib 132 which extends outwardly from the surface 131. The surface of the inner recovery tip 122 includes a number of rib-like channels 136 which are adapted to receive the rib 132 formed on the recovery sheath 120. In a similar manner, these channels 136 help to increase the frictional contact between these two components since a certain amount of force must first be applied to move the rib 132 into the second and third channels 136 located on the inner recovery tip. Additional channels can be added if additional resistive force is to be maintained. After the force is sufficient to extend the rib past the last channel, the inner recovery tip 122 will then retract fully into the lumen 124 of the recovery sheath 120. Again, this is just one of a number of different simple frictional mechanisms which can be utilized in accordance with these components to increase the amount of force needed to retract the inner recovery tip 122 into the recovery sheath 120.

Friction between the restraining sheath and medical component can be reduced by applying a coat of silicone lubricant, such as Microglide®, to the inside surface of the restraining sheath before the sheath is placed over the medical component.

In view of the foregoing, it is apparent that the devices of the present invention substantially enhance the safety and efficiency of delivering and recovering embolic protection devices, and other medical devices, in a patient's vasculature. Further modifications and improvements may additionally be made to the system and method disclosed herein without departing from the scope of the present invention. Accordingly, it is not intended that the invention be limited, except as by the appended claims.

What is claimed is:

1. A restraining device for maintaining a self-expanding medical device on a delivery device, comprising:
a restraining sheath having an expandable housing portion adapted to receive and maintain the self-expanding medical device in a collapsed condition on the delivery device, the expandable housing portion being adapted to move between a contracted position and expanded position, the housing portion having sufficient column strength to maintain the self-expanding medical device in its collapsed condition on its delivery device, wherein:
the expandable housing portion is made primarily from an elastic material which is movable between the contracted position and expanded position and includes at least one reinforcing member associated therewith which provides additional column strength to the housing portion but does not interfere with the expansion or contraction of the housing portion.

2. The restraining device of claim 1, further including:
a plurality of reinforcing members associated with the expandable housing portion to provide additional column strength to the housing portion.

3. The restraining device of claim 2, wherein:
the reinforcing members extend substantially along the length of the expandable housing portion but do not interfere with the expansion of the elastic material.

4. The restraining device of claim 3, wherein:
the reinforcing members are elongated bar-like members made from a material having high stiffness.

5. The restraining device of claim 2, wherein:
the reinforcing member is made from a material selected from a group including stainless steel, polymeric material, and nitinol.

6. The restraining device of claim 5, wherein:
the reinforcing members are loaded with a material having high radiopacity.

7. The restraining device of claim 2, wherein:
the reinforcing members are disposed within the elastic material forming the expandable housing portion.

8. The restraining device of claim 2, wherein:
the reinforcing members are attached to the surface of the expandable housing portion.

9. The restraining device of claim 2, wherein:
each reinforcing member is disposed along the expandable housing portion to provide additional column strength to the housing portion but does not interfere with the expansion of the housing portion.

10. The restraining device of claim 1, wherein:
the elastic material is selected from a group of materials which includes silicone, polyurethane, polyisoprene, and lower durometer PEBAX.

11. The restraining device of claim 1, wherein:
the expandable housing portion is made from a substantially tubular-shaped material which is highly elastic and includes a plurality of reinforcing members disposed within the tubular elastic material to provide additional column strength to the housing portion.

12. The restraining device of claim 1, wherein:
the expandable housing portion includes a low expansion section with at least one expansion member disposed within the low expansion section to provide the elasticity needed to move the housing portion between the contracted position and expanded position.

13. The restraining device of claim 1, wherein:
the expandable housing portion includes a plurality of low expansion sections and a plurality of expansion members disposed between low expansion sections.

14. The restraining device of claim 13, wherein:
the low expansion sections are made from a material loaded with a material having high radiopacity.

15. The restraining device of claim 13, wherein:
the expansion members are made from an elastic material selected from a group which includes polyurethane, silicone, polyisoprene and lower durometer PEBAX.

16. The restraining device of claim 15, wherein:
the low expansion sections are made from a material selected from a group including cross-linked HDPE, polyolefin and polyamide.

17. The restraining device of claim 13, wherein:
the expansion members extend longitudinally along the length of the expandable housing portion.

18. The restraining device of claim 17, wherein:
the expansion members include means for preventing the low expansion sections from tearing as the expandable housing portion expands from the contracted position to the expanded position.

19. A restraining device for maintaining a self-expanding medical device on a delivery device, comprising:
a restraining sheath having an expandable housing portion adapted to move between a contracted position and an expanded position and to maintain the self-expanding medical device in a collapsed condition on the delivery device, and a reinforcing member associated with the expandable housing portion to cooperatively provide sufficient strength to the expandable housing portion to maintain the self-expanding medical device in its collapsed condition on its delivery device without the reinforcing member interfering with the ability of the expandable housing portion to move between the contracted and expanded positions.

20. The restraining device of claim 19, further including:
a plurality of reinforcing members associated with the expandable housing portion to provide additional column strength to the housing portion but which do not interfere with the ability of the expandable housing to move between the contracted and expanded positions.

21. The restraining device of claim 19, wherein:
the reinforcing member is embedded in the wall which forms the expandable housing portion.

22. The restraining device of claim 19, wherein:
the reinforcing member is an elongated bar-like member made from a material having a stiffness higher than the stiffness of the material used to form the expandable housing portion.

23. The restraining device of claim 19, wherein:
the expandable housing portion is made from an elastic material selected from a group of materials which includes silicone, polyurethane, polyisoprene, and low durometer PEBAX.

24. The restraining device of claim 19, wherein:
the reinforcing member is made from a material selected from a group including stainless steel, polymeric material, and nitinol.

25. The restraining device of claim 19, wherein:
the reinforcing member is loaded with a material having high radiopacity.

26. The restraining device of claim 19, wherein:
the expandable housing portion is made from a substantially tubular-shaped material which is highly elastic and includes a plurality of reinforcing members disposed within the tubular elastic material to provide additional column strength to the housing portion.

27. The restraining device of claim 19, wherein:
the reinforcing member is molded within the material used to form the expandable housing portion.

28. The restraining device of claim 19, wherein:
the reinforcing member is attached to the surface of the expandable housing portion.

29. The restraining device of claim 19, wherein:
the reinforcing member helps to bias the expandable housing portion in the contracted position.

* * * * *